United States Patent [19]

Di Schiena

[11] Patent Number: 4,657,923
[45] Date of Patent: Apr. 14, 1987

[54] ECONAZOLE-ACEXAMIC ACID ADDITION COMPOUND HAVING ANTIMYCOTIC, CICATRIZING AND ANTIINFLAMMATORY ACTIVITY

[75] Inventor: Michele G. Di Schiena, Trezzano Sul Naviglio, Italy

[73] Assignee: Chinoin S.p.A., Milan, Italy

[21] Appl. No.: 760,359

[22] Filed: Jul. 30, 1985

[51] Int. Cl.⁴ .................. A61K 31/415; C07D 233/60
[52] U.S. Cl. .................................... 514/399; 548/341
[58] Field of Search ...................... 548/341; 514/399

[56] References Cited

U.S. PATENT DOCUMENTS 3,717,655  2/1973  Godefroi et al. .................. 548/341

Primary Examiner—Richard A. Schwartz
Attorney, Agent, or Firm—Walter H. Schneider

[57] ABSTRACT

The addition compound between econazole and acexamic acid is hereinafter described.

The novel compound has valuable antimycotic, antiinflammatory and cicatrizing properties, which make it suitable for the preparation of pharmaceutical compositions for topical use, particularly for vaginal and urethral use.

The compound is useful for human and veterinary formulations.

2 Claims, No Drawings

ECONAZOLE-ACEXAMIC ACID ADDITION COMPOUND HAVING ANTIMYCOTIC, CICATRIZING AND ANTIINFLAMMATORY ACTIVITY

The present invention relates to the novel addition compound between econazole and acexamic acid, having formula (I)

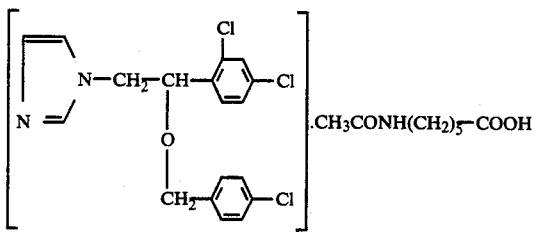

The present invention relates also to processes for preparing compound (I) as well as pharmaceutical compositions containing compound (I) as the active principle, particularly compositions for vaginal and urethral use.

Econazole has been known for a long time to be valuable antimycotic drug, particularly useful in the treatment of gynecological diseases (see, e.g., J. Med. Chem. 12 (1969) 784).

Econazole is commonly used in therapy for topical use, in form of addition compound with nitric acid. The administration of nitrate compounds for topical route is known to present some dangers, due to possible formation of nitrosamine, which are cancerogenic compounds.

The mechanism of formation of nitrosamines seems in fact to involve nitrocompounds and biological amines as well as amines present in pharmaceutical compositions for topical use (such as triethanolamine, etc.).

Acexamic acid, or ε-acetamidocaproic acid, is a well known antiinflammatory and cicatrizing drug, due to its favourable effect on connective tissue and epithelia, used in dermatology for healing sores and wounds ("Repertorio Terapeutico", 6th Ed.).

Compound (I) according to the present invention, while exhibiting a therapeutical action which is substantially superimposable to those of the single components thereof, has the peculiar advantage of a higher therapeutical safety, since any possible production of such cancerogenic compounds as nitrosoamines is avoided, which production can, on the contrary, occur in case of use of the addition compound between econazole and nitric acid.

The novel compound (acenazole) exhibits toxicity and hysto-damaging activity which are equal to or lower than those of its single components.

Therefore the novel compound (acenazole) is therapeutically useful in the treatment of those mycotic diseases treated with econazole, and also of mycotic diseases in which skin or mucosal lesions and irritative or phlogistic factors are present.

Compound I is particularly useful in the treatment of vaginal and urethal mycosis.

The compounds of the invention may be administered in form of conventional topical compositions, such as powders, solutions, ointments, gels, creams; impregnated tissues, sanitary towels or napkins; dermatologic milks and soaps; collutoria, otologic-drops, eye-drops; preparations for scalp mycosis, shampoos, lotions and creams; urethral suppositories, vaginal capsules, creams and gels, vaginal washings, preparations for the direct introduction in vagina by means of cannula supplying devices with manual or mechanic pressure (spray foam).

Said formulations may optionally contain other compounds having pharmacological properties (pharmaceutical combinations), and pharmaceutically acceptable carriers and excipients, such as surfactants, emulsifiers, pH regulating agents, preservers, perfumes, etc.

The compound according to the invention may be prepared in various ways, for example by reacting econazole with acexamic acid, in anhydrous or partially hydrated solvents, such as methanol, ethanol, isopropanol, acetone, etc.

Econazole and acexamic acid are reacted in equimolecular ratios or in an excess up to 5% of acexamic acid.

Temperature is not critical, as it can range from 0° to 100° C., preferably from 20° to 50° C.

The compound may be recovered according to conventional techniques, such as crystallization, precipitation by means of non-solvents, evaporation (possibly under vacuum) and spray-dry.

The following examples further illustrate the invention, without limiting it.

EXAMPLE 1

38 Grams (0.1 mol) of econazole were added to 250 ml of 30% aqueous acetone, to obtain a clear solution having pH~8.5 (Solution A.).

17.3 Grams (0.1 mol) of acexamic acid were added to 250 ml of 30% aqueous acetone, to give a clear solution having pH~4.

The two obtained solutions were mixed to give a mixture having pH~6. The mixture was concentrated under vacuum to small volume, the residue was taken up in 300 ml of acetone. Solvent was evaporated off, the oily residue was recovered, left to crystallize and dried (air, 30° C.).

Yield: 55 g; m.p. 60°–62° C. TLC analysis and I.R. analysis prove the purity and nature of the obtained compound.

EXAMPLE 2

51.9 Grams of acexamic acid were suspended in 250 ml of acetone. A clear solution of 114 g of econazole in 250 ml of acetone was added under strong stirring, at 40° C. After some time a complete solution was obtained, which was filtered. The residue was evaporated under vacuum at 50° C. in order to remove the solvent. An oily residue was obtained which crystallized upon cooling. The obtained product was dried (air, 30° C.) to give 164 g of the desired compound, analytically corresponding to that of Example 1.

EXAMPLE 3

Cream for vaginal use (ingredient for 100 g of preparation).

To 1.25 g of Compound I, vaseline oil, emulsifier, water and a preserver, q.s. to 100 g, are added.

EXAMPLE 4

Ovules for vaginal use (ingredients for one 3 g ovule).

The following excipients are added to 0.063 g of Compound I: vaseline oil, thick vaseline. Coating: gelatine, glycerine, zinc oxyde, preservative agent.

EXAMPLE 5

Suppositories for urethral use (ingredients for one 2 g suppository).

Compound I 0.200 g; excipients and coating agents q.s.

EXAMPLE 6

Dermatological powders.

Compound I 1.5 g; excipients: rice starch, talc, zinc oxyde, q.s.

EXAMPLE 7

Dermatological cream (ingredients for 100 g).

Compound I 1.25 g; excipients: polyethylene-glycole 1000 monocetyl ester, cetyl alcohol, stearyl alcohol, vaseline, vaseline oil, distilled water q.s.

I claim:

1. The addition compound between econazole and acexamic acid, of formula (I):

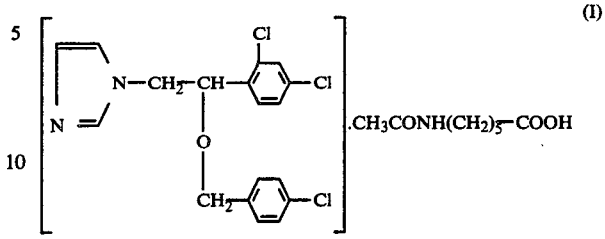

2. A pharmaceutical composition having antimycotic, cicatrizing and antiimflammatory activity for topical administration in human and veterinary use comprising as the principal active ingredient an effective amount of a compound according to claim 1 in admixture with a pharmaceutically acceptable carrier.

* * * * *